(12) United States Patent
Scallon et al.

(10) Patent No.: US 7,427,471 B2
(45) Date of Patent: Sep. 23, 2008

(54) MODIFIED "S" ANTIBODIES

(75) Inventors: Bernard J. Scallon, Wayne, PA (US); Ann Cai, West Chester, PA (US); Michael Naso, Philadelphia, PA (US)

(73) Assignee: Centocor, Inc., Malvern, PA (US)

( * ) Notice: Subject to any disclaimer, the term of this patent is extended or adjusted under 35 U.S.C. 154(b) by 291 days.

(21) Appl. No.: 10/454,948

(22) Filed: Jun. 5, 2003

(65) Prior Publication Data

US 2003/0232046 A1    Dec. 18, 2003

Related U.S. Application Data

(60) Provisional application No. 60/388,896, filed on Jun. 14, 2002.

(51) Int. Cl.
| | | |
|---|---|---|
| C12Q 1/68 | (2006.01) | |
| A61K 39/395 | (2006.01) | |
| C07K 16/00 | (2006.01) | |
| C07H 21/04 | (2006.01) | |
| C12N 15/00 | (2006.01) | |
| C12N 5/06 | (2006.01) | |
| C12P 21/06 | (2006.01) | |

(52) U.S. Cl. .................. 435/6; 424/130.1; 530/388.23; 536/23.53

(58) Field of Classification Search ...... 435/6; 424/130.1; 530/388.23; 536/23.53
See application file for complete search history.

(56) References Cited

U.S. PATENT DOCUMENTS

| 644,792 | A | * | 3/1900 | Gray et al. ............... 126/58 |
| 5,834,597 | A | * | 11/1998 | Tso et al. ............. 530/387.3 |
| 5,959,177 | A | | 9/1999 | Hein et al. |
| 6,045,795 | A | | 4/2000 | Ulevitch et al. |
| 6,284,536 | B1 | | 9/2001 | Morrison et al. |

FOREIGN PATENT DOCUMENTS

| WO | WO 00/09560 | * | 2/2000 |
| WO | WO 00/09560 A2 | | 2/2000 |

OTHER PUBLICATIONS

Cavacini et al. (J. Immunol. 155:3638-3644 (1995)).*
Burgess et al, (Journal of Cell Biology vol. 111 Nov. 1990 2129-2138).*
Lazar et al (Molecular and Cellular Biology Mar. 1988 vol. 8 No. 3 1247-1252).*
Schwartz et al, (Proc Natl Acad Sci USA vol. 84:6408-6411 (1987).*
Lin et al Biochemistry USA vol. 14:1559-1563 (1975).*
Ibragimova and Wade (Biophysical Journal, Oct. 1999, vol. 77, pp. 2191-2198).*
Dangl et al. (EMBO J. 7(7):1989-1994 (1988).*
Batra et al. (Molecul. Immunol. 30(4):379-386 (1993).*
Schneider et al. (PNAS, USA. 85:2509-2513 (1988).*
Doring et al. (Molecul. Immunol. 31:1059-1067 (1994).*
Stratagene Catalogue (1988).*
Dangl, J.T. et al. Segmental flexibility and complement fixation of genetically engineered chimeric human, rabbit and mouse antibodies. The EMBO Journal. vol. 7, No. 7, pp. 1989-1994.
Cavacini, L.A. et al. Influence of heavy chain constant regions on antigen binding and HIV-1 neutralization by a human monoclonal antibody. The Journal of Immunology, 1995, vol. 155, pp. 3638-3644.
Roux, H.K. et al. Comparisons of the ability of human IgG3 hinge mutants, 1gM, IgE, and IgA2, to form small immune complexes; A role for flexibility and geometry. The Journal of Immunology, 1998, vol. 161, pp. 4083-4090.
Greenwood et al, "Structural motifs involved in human IgG antibody effector functions,m" Eur. J. Immunol. 1993, 23:1098-1104.
Greenwood, et al., "Engineering Multiple-Domain Forms of the Therapeutic Antibody CAMPATH-1H: Effects on Complement Lysis," Therapeutic Immunology, 1: 247-255 (1994).
Ma, et al., "Assembly of monoclonal antibodies with IgG1 and IgA heavy chain domains in transgenic tobacco plants," European Journal of Immunology, 24: 131-138 (1994).
Isogai, et al., "Therapeutic effect of anti-TNF-α antibody and levofloxacin (LVFX) in a mouse model of enterohemorrhagic *Escherichia coli* O157 infection," Comparative Immunology, Microbiology & Infectious Diseases, 24: 217-231 (2001).
Scallon, et al., "Addition of an extra immunoglobulin domain to two anti-rodent TNF monoclonal antibodies substantially increased their potency," Molecular Immunology, 41: 73-80 (2004).
Kadokami, et al., "Anti-Tumor Necrosis Factor-α Antibody Limits Heart Failure in a Transgenic Model," Circulation, 104: 1094-1097 (2001).
Supplementary European Search Report dated Mar. 12, 2007.

* cited by examiner

*Primary Examiner*—David J. Blanchard
*Assistant Examiner*—Lynn Bristol
(74) *Attorney, Agent, or Firm*—Kenneth J. Dow

(57) ABSTRACT

The invention relates to the field of antibodies, and particularly to modified antibodies, methods of preparing modified antibodies and uses thereof. More particularly, the invention relates to the preparation of more active IgG antibodies by the addition of an extra immunoglobulin domain to the constant region.

13 Claims, 6 Drawing Sheets

Figure 1:
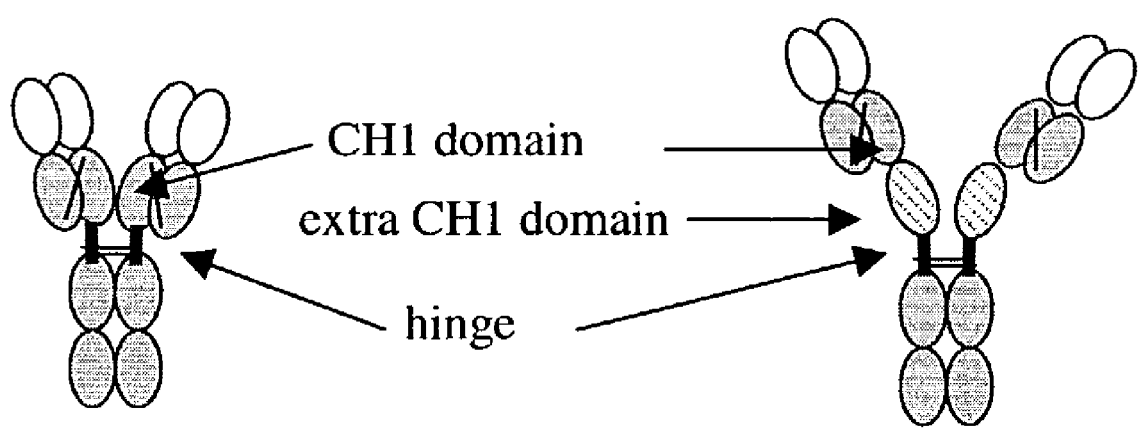

```
muG2A   KTTAPSVYPL APVCGDTTGS SVTLGCLVKG YFPEPVTLTW NSGSLSSGVH         muG2a CH1
S-Ab    KTTAPSVYPL APVCGDTTGS SVTLGCLVKG YFPEPVTLTW NSGSLSSGVH 51                                                    100
muG2A   TFPAVLQSDL YTLSSSVTVT SSTWPSQSIT CNVAHPASST KVDKKIA
S-Ab    TFPAVLQSDL YTLSSSVTVT SSTWPSQSIT CNVAHPASST KVDKKIAKTT 101                                                   150
S-Ab    PPSVYPLAPG SAAQTNSMVT LGCLVKGYFP EPVTVTWNSG SLSSGVHTFP         muG1 CH1

151                                                   200
                                                      PRGPTI
muG2A
S-Ab    AVLESDLYTL SSSVTVPSSP RPSETVTCNV AHPASSTKVD KKIEPRGPTI         muG2a hinge 201                                                   250
muG2A   KPCPPCKCPA PNLLGGPSVF IFPPKIKDVL MISLSPIVTC VVVDVSEDDP         muG2a CH2
S-Ab    KPCPPCKCPA PNLLGGPSVF IFPPKIKDVL MISLSPIVTC VVVDVSEDDP 251                                                   300
muG2A   DVQISWFVNN VEVHTAQTQT HREDYNSTLR VVSALPIQHQ DWMSGKEFKC
S-Ab    DVQISWFVNN VEVHTAQTQT HREDYNSTLR VVSALPIQHQ DWMSGKEFKC 301                                                   350
muG2A   KVNNKDLPAP IERTISKPKG SVRAPQVYVL PPPEEEMTKK QVTLTCMVTD         muG2a CH3
S-Ab    KVNNKDLPAP IERTISKPKG SVRAPQVYVL PPPEEEMTKK QVTLTCMVTD 351                                                   400
muG2A   FMPEDIYVEW TNNGKTELNY KNTEPVLDSD GSYFMYSKLR VEKKNWVERN
S-Ab    FMPEDIYVEW TNNGKTELNY KNTEPVLDSD GSYFMYSKLR VEKKNWVERN 401                  426
muG2A   SYSCSVVHEG LHNHHTTKSF SRTPGK
S-Ab    SYSCSVVHEG LHNHHTTKSF SRTPGK MuG2A   SEQ ID NO. 1
S-Ab:   SEQ ID NO. 2
```

FIGURE 2

MODIFIED "S" ANTIBODIES

CROSS REFERENCE TO RELATED APPLICATION

This application claims the benefit of provisional application Ser. No. 60/388,896 filed Jun. 14, 2002.

BACKGROUND OF THE INVENTION

1. Field of the Invention

The invention relates to the field of antibodies, and particularly to modified antibodies, methods of preparing modified antibodies and uses thereof. More particularly, the invention relates to the preparation of more active IgG antibodies by the addition of an extra immunoglobulin domain to the constant region.

2. Background and Related Art

For several decades antibodies have been indispensable in research and diagnosis and more recently in the therapeutic treatment of diseases due to their specific binding properties and high stability. Monoclonal antibodies were initially produced by fusing a chosen B cell line with an immortal myeloma cell line to produce hybridomas, immortal cells that secrete only the selected antibody type of the selected B cell clone. The use of recombinant DNA technologies has enabled new methods of producing antibodies as well as the design of new antibody constructs.

Structurally, each antibody is formed by the interaction of two identical "heavy" chains and two identical "light" chains, all of which combine to form a Y shape molecule (the heavy chains span the entire Y, and the light chains the two arms only). An immunoglobulin G antibody molecule contains complementary determining regions (CDRs) which determine antigen binding, constant regions that determine effector function and framework regions. An antibody construct can include any protein or peptide containing molecule that comprises at least a portion of an immunoglobulin molecule, such as but not limited to at least one CDR of a heavy or light chain or a ligand binding portion thereof, a heavy chain or light chain variable region, a heavy chain or light chain constant region, a framework region, or any portion thereof. An antibody fragment can include the fragment of the immunoglobulin molecule known as the Fab containing the CDR antigen binding site, generated by cleavage of the antibody with the protease papain which cuts at the "hinge" region of the Y shaped antibody molecule producing two Fab fragments. An antibody can include or be derived from any mammal, such as but not limited to a human, a mouse, a rabbit, a rat, a rodent, a primate, or any combination thereof.

Antibodies (Abs) to human antigens usually do not cross-react with the corresponding rodent antigen, with the exception being some Abs to antigens that are highly conserved in structure. Consequently, while developing an Ab to a human target, there is often a need for a separate Ab to the rodent antigen for the purpose of performing preclinical studies in rodents. Because such studies are done to reveal what could be expected to happen in humans treated with the anti-human Ab, it is important that the anti-rodent "surrogate" Ab being used in the animal studies is similar to the anti-human Ab in as many characteristics as possible. Such characteristics for an Ab may include affinity or avidity for antigen, relative neutralization potency, isotype and the associated Fc-mediated immune effector functions (e.g. complement fixation), pharmacokinetic behavior, and ability to form immune complexes with its soluble target antigen. Because there are usually few choices of Abs that can serve as a suitable surrogate for animal studies, it is often very difficult, if not impossible, to find the perfect surrogate Ab. It may be that the two most important characteristics, neutralization of rodent antigen bioactivity and analogous IgG isotypes, are considered sufficient for a surrogate Ab.

While it is possible to develop a rodent antibody that neutralizes the corresponding rodent antigen, it is often necessary to change the antibody isotype to satisfy one criterion for it serving as a surrogate Ab for the human antibody: having its isotype be the functional counterpart isotype to the human antibody. In doing so, it has been shown that the resulting modified antibody may demonstrate in vivo bioactivity in vitro and show complement-fixing activity against rodent antigen-expressing cells in vitro. However, the amount of the modified antibody required to block a given amount of antigen bioactivity can be much higher than than the amount of human antibody required to block the same amount of human antigen bioactivity. Furthermore, the modified rodent antibody can be less potent than the original rodent antibody against the rodent antigen.

This difference in activity and potency can be the result of a fundamental difference between the way the modified antibody and the human antibody bind antigen. Whereas both arms of the human antibody can simultaneously bind two different antigen molecules, the binding of one arm of the dimeric modified antibody molecule to one antigen molecule can prevent the second arm from binding to a second antigen molecule. The modified antibody may be functionally monovalent whereas the natural antibody may be bivalent. Further, by virtue of its ability to bind two molecules of a target that itself may be a homopolymer (for example, TNF is a homotrimer) that can be bound by more than one molecule, the natural antibody may be capable of forming higher order complexes with the target molecule. In contrast, because of its inability to bind more than one target molecule simultaneously, the modified antibody would not be capable of forming higher order complexes with the target molecule. The relative stability of the natural antibody/target molecule complexes and the modified antibody/target molecule complexes would therefore be expected to be dramatically different, since most molecules of the natural antibody would be bound to the complex bivalently and have a very slow dissociation rate, whereas each molecule of the modified antibody would be bound monovalently and therefore have a much faster dissociation rate. Because dissociation of the modified antibody from the target results in a target molecule that is free and bioactive, the result would be large differences in neutralization potencies between natural and modified antibodies.

In addition to neutralization potencies, the difference in the size and complexity of the Ab/target molecule complexes would also be expected to affect such activities as serum clearance rates and Fc receptor binding affinities with concomitant cell activation.

Thus, in engineering modified antibodies it is sometimes desirable to ensure that the resulting construct is functionally bivalent by virtue of its ability to bind two molecules of a target. In the case of an antigen that is itself a homopolymer that can be bound by more than one antibody molecule, it is desirable to have a construct that is capable of forming higher order complexes with the antigen in order to achieve maximum potency and stability of the antibody/antigen complex.

Thus, there is a need for a method of engineering antibodies to provide added flexibilty and spatial distance to allow for multiple binding valencies and complex formations in antigen/antibody binding resulting in both favorable binding characteristics and neutralization capabilities of the antibody construct.

SUMMARY OF THE INVENTION

The invention described here is a modified Ab (an 'S' Ab) that confers added flexibility to, and spatial distance between, the two Fab domains by incorporating an extra constant region immunoglobulin (Ig) domain into the constant region of a normal Ab.

Figure 3:
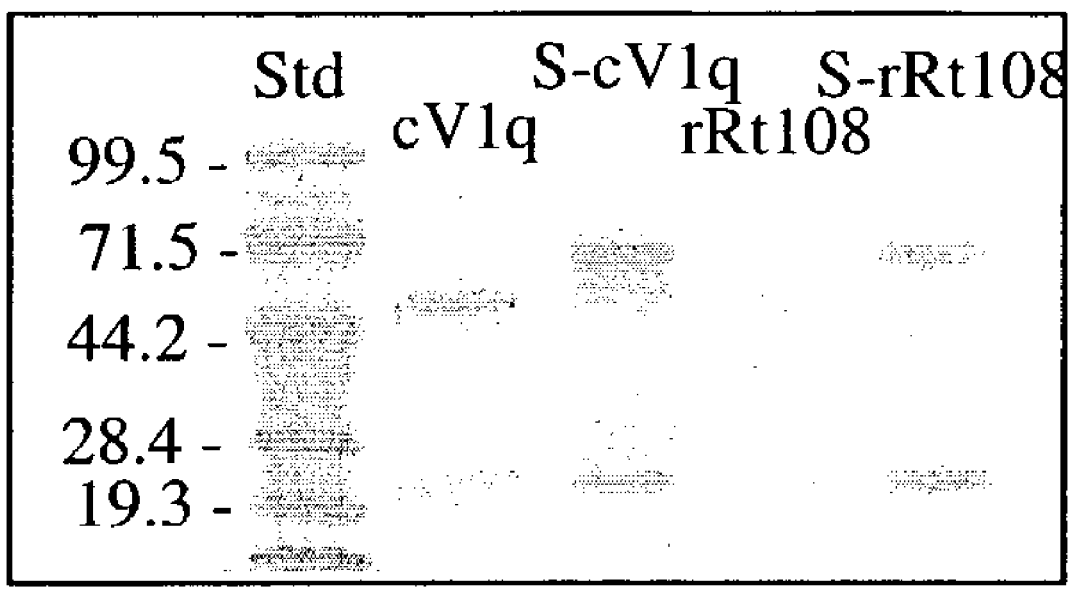

Thus, in one aspect, the invention relates to a method of providing added flexibility to, and spatial distance between, Fab domains of an antibody by incorporating an extra constant region immunoglobulin (Ig) domain into the constant region of an antibody. The resulting construct is referred to as an 'S' antibody. The S antibodies prepared by the method of the invention demonstrate enchanced neutralization ability over the unmodified antibodies. As shown in the following examples, the rodent anti-TNF S-Abs prepared in accordance with the invention, S-cV1q and S-rRt108, are respectively 200-fold and 20-fold more effective at neutralizing TNF bioactivity than the original cV1q and rRt108 Abs.

The present invention provides, in another aspect, isolated nucleic acid molecules comprising, a polynucleotide encoding the aforementioned S antibodies and at least one specified sequence, domain, portion or variant thereof. The present invention further provides recombinant vectors comprising anti-S antibody nucleic acid molecules, host cells containing such nucleic acids and/or recombinant vectors, and methods of making and/or using such antibody nucleic acids, vectors and/or host cells.

The present invention also provides at least one method for expressing at least one S antibody in a host cell, comprising culturing a host cell as described herein under conditions wherein at least one S antibody is expressed in detectable and/or recoverable amounts. The host cell may be selected from COS-1, COS-7, HEK293, BHK21, CHO, BSC-1, Hep G2, Ag653, SP2/0, HeLa, myeloma, or lymphoma cells, or any derivative, immortalized or transformed cell thereof. Also provided is a method for producing at least one S antibody, comprising translating the antibody encoding nucleic acid under conditions in vitro, in vivo or in situ, such that the S antibody is expressed in detectable and/or recoverable amounts.

The present invention also provides at least one composition comprising both an isolated S antibody encoding nucleic acid and/or antibody as described herein and a suitable carrier or diluent. The carrier or diluent may be pharmaceutically acceptable, according to known carriers or diluents. The composition may also comprise at least one further compound, protein or composition. The composition may also comprise an effective amount of at least one compound or protein selected from a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog a cytotoxic or other anti-cancer agent, an antimetabolite such as methotrexate, an anti-proliferative agent, a cytokine, or a cytokine antagonist.

The present invention further provides at least one method or composition for administering a therapeutically effective amount of an S antibody of the invention to modulate or treat at least one disease condition in a cell, tissue, organ, animal or patient, prior to, subsequent to, or during a related condition, as known in the art and/or as described herein.

The present invention also provides at least one composition, device and/or method for the delivery of a therapeutically or prophylactically effective amount of at least one S antibody, according to the present invention.

The present invention further provides at least one S antibody method or composition, for diagnosing at least one disease condition in a cell, tissue, organ, animal or patient, prior to, subsequent to, or during a related condition, as known in the art and/or as described herein.

Also provided is a medical device, comprising at least one isolated S antibody of the invention, wherein the device is suitable for contacting or administering the S antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is an article of manufacture for human pharmaceutical or diagnostic use, comprising packaging material and a container comprising a solution or a lyophilized form of at least one isolated S antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

Also provided is a method for producing at least one isolated S antibody of the present invention, comprising a host, transgenic animal, transgenic plant or plant cell capable of expressing the antibody in recoverable amounts. Further provided in the present invention is at least one S antibody produced by the above method.

The present invention further provides any invention described herein.

BRIEF DESCRIPTION OF THE FIGURES

In the drawings that form a portion of the specification:

FIG. 1 is a schematic comparison of normal Ab structure with S-Ab structure. V regions are shown in white and constant regions in blue. The extra CH1 domain from a mouse IgG1 Ab is shown with hatched lines.

FIG. 2 is an amino acid sequence comparison between the heavy chain constant region of a normal murine IgG2a (muG2a) (SEQ. ID. No. 1) and an S-Ab of the present invention (SEQ. ID. No. 2). Amino acids are shown in single-letter code. The extra CH1 domain in the S-Ab extends from amino acids 98-194. Constant region sequence is shown in blue. $Cys^{14}$ (underlined) disulfide bonds with the LC.

FIG. 3 is an SDS-polyacrylamide gel analysis comparing the migration of the normal and S-Ab heavy and light chains. Each protein sample was reduced with β-mercaptoethanol and passed through a 5-15% gradient polyacrylamide gel by electrophoresis. Following electrophoresis, proteins in the gel were stained with Coomassie Blue stain. Sizes of molecular weight standards are shown in kDa on the left. This particular prep of S-cV1q contained some bovine IgG.

Figure 4:
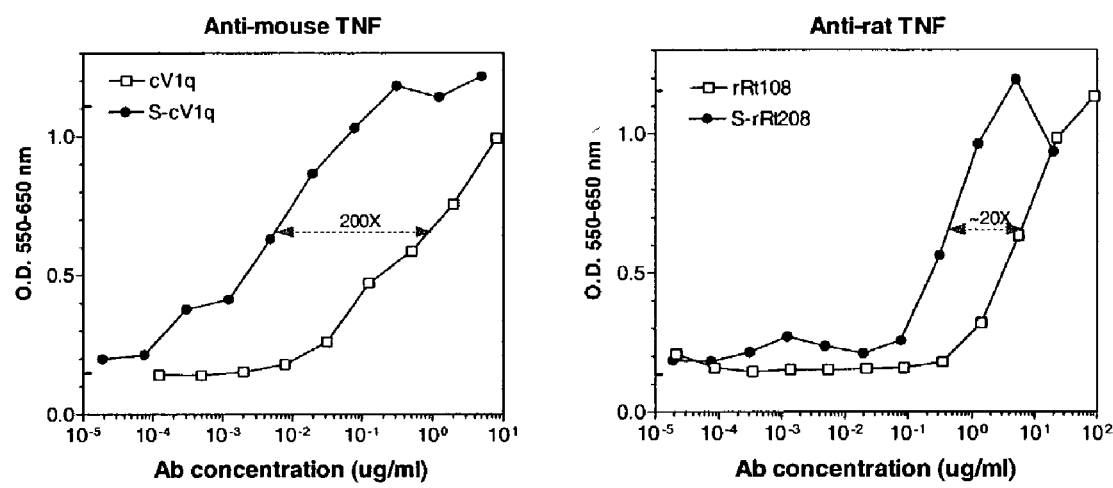

FIG. 4 is a graph showing the results from a WEHI cell cytotoxicty assay. Varying amounts of Ab were preincubated with either mouse TNF (left) or rat TNF (right) and the mixture added to WEHI-164 cells to have a final concentration of 10 pg/ml TNF. The Ab/TNF/cell mixture was incubated at 37° C. for 16 hours and then cell viability was quantitated by adding MTT dye and determining $OD_{550-650}$ values. A high OD indicates live cells. Because the S-Abs have a molecular weight that's 30 kDa more than the normal Abs, the differences between the normal and S-Abs on a molar basis would be greater than what is shown (240-fold vs 200-fold for cV1q).

Figure 5:
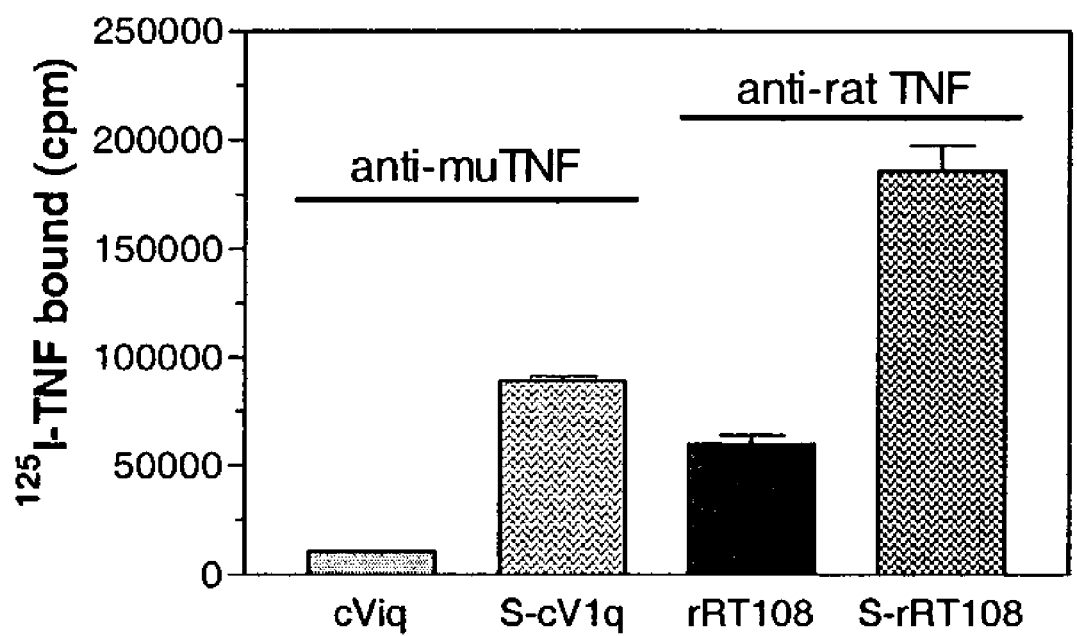

FIG. 5 is a graph showing the results of a binding assay to compare ability of normal and S-Abs to bind two TNF molecules simultaneously. EIA plates were coated with 2 μg/ml of mouse or rat TNF. Mouse TNF-coated wells were incubated with 100 μg/ml of either cV1q or S-cV1q. Rat TNF-coated wells were incubated with 100 μg/ml of either rRt108 or S-rRt108. Unbound Ab was removed by washing and 2 μg/ml of $^{125}$I-labeled mouse or rat TNF was added. Unbound TNF was removed by washing and the number of counts bound was determined using a gamma counter.

Figure 6:
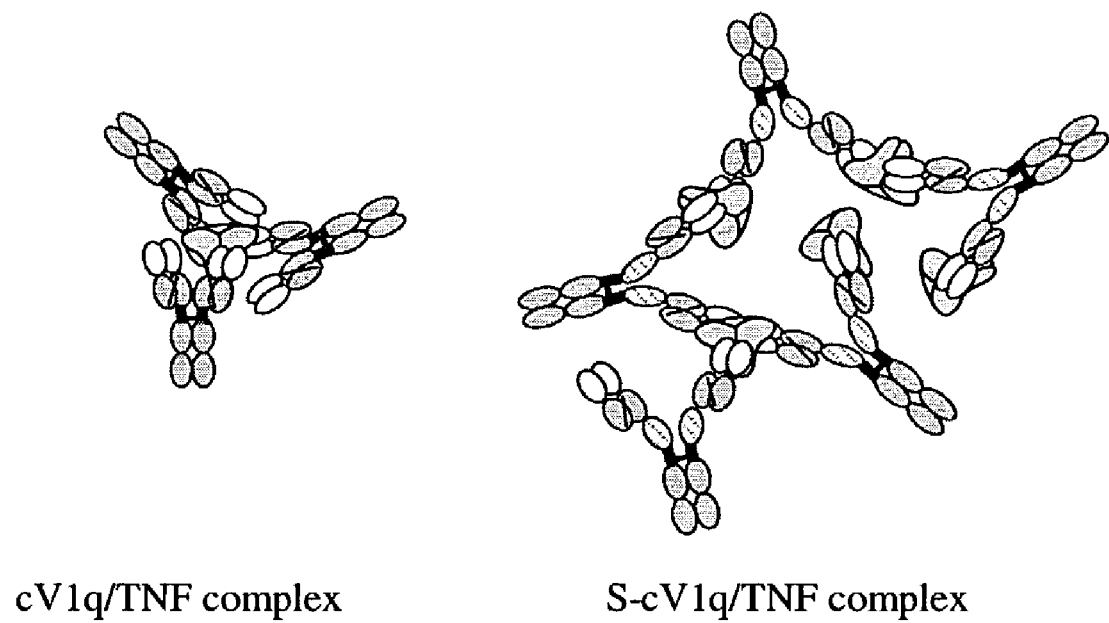

FIG. 6 is a schematic depiction of how S-cV1q/muTNF complexes are believed to differ from cV1q/muTNF complexes. Note that unlike cV1q, each molecule of S-cV1q can bind two TNF molecules simultaneously. The increased potency of S-cV1q is believed to be due to its bivalent binding to complexes of TNF, which is the reason for a much slower dissociation rate from TNF compared to cV1q. The S-cV1q/muTNF complexes would be expected to be very similar or identical to the cA2/huTNF complexes (see FIG. 1).

DETAILED DESCRIPTION OF THE INVENTION

A. Citations

All publications or patents cited herein are entirely incorporated herein by reference, as they show the state of the art at the time of the present invention and/or provide description and enablement of the present invention. Publications refer to any scientific or patent publications, or any other information available in any media format, including all recorded, electronic or printed formats. (The following references are entirely incorporated herein by reference: Ausubel, et al., ed., *Current Protocols in Molecular Biology*, John Wiley & Sons, Inc., NY, N.Y. 1987-2001; Sambrook, et al., *Molecular Cloning: A Laboratory Manual*, 2$^{nd}$ Edition, Cold Spring Harbor, N.Y. 1989; Harlow and Lane, *Antibodies:Aa Laboratory Manual*, Cold Spring Harbor, N.Y. 1989; Colligan, et al., eds., *Current Protocols in Immunology*, John Wiley & Sons, Inc., NY 1994-2001; Colligan et al., *Current Protocols in Protein Science*, John Wiley & Sons, NY, N.Y., 1997-2001.)

B. Definitions

Unless otherwise defined, scientific and technical terms used in connection with the present invention shall have the meanings that are commonly understood by those of ordinary skill in the art.

Furthermore, unless otherwise required by context, singular terms shall include pluralities and plural terms shall include the singular. Generally, nomenclatures utilized in connection with, and in techniques of, cell and tissue culture, molecular biology, protein and oligo- or polynucleotide chemistry and hybridization described herein are those well known and commonly used in the art. Standard techniques are used for recombinant DNA, oligonucleotide synthesis, tissue culture, and transformation (e.g., electroporation, lipofection).

Enzymatic reactions and purification techniques are performed according to the manufacturer's specifications, as commonly accomplished in the art, or as described herein. The foregoing techniques and procedures are generally performed according to conventional methods well known in the art and as described in various general and more specific references that are cited and discussed. (Seee.g., Sambrook et al. *Molecular Cloning: A Laboratory Manual*, 2$^{nd}$ ed., Cold Spring Harbor Laboratory Press, Cold Spring Harbor, N.Y. 1989, which is incorporated herein by reference.) The nomenclatures utilized in connection the laboratory procedures and techniques of analytical, synthetic organic, medicinal and pharmaceutical chemistry, described herein, are those well known and commonly used in the art. Standard techniques are used for chemical syntheses, chemical analyses, pharmaceutical preparation, formulation, and the delivery and treatment of patients.

All scientific and technical terms used in this application have meanings commonly used in the art unless otherwise specified. As used in this application, the following words or phrases have the following meanings:

"Antibody" or "antibody peptide(s)" refers to an intact antibody, or a binding fragment thereof, that competes with the intact antibody for specific binding. Binding fragments are produced by recombinant DNA techniques, or by enzymatic or chemical cleavage of intact antibodies. Binding fragments include Fab,Fab', F(ab1) 2, Fv, and single-chain antibodies. An antibody other than a "bispecific" or "bifunctional" antibody is understood to have each of its binding sites identical. An antibody substantially inhibits adhesion of a receptor to a counter receptor when an excess of antibody reduces the quantity of receptor bound to counter receptor by at least about 20%, 40%, 60% or 80%, and more usually, greater than about 85% (as measured in an in vitro competitive binding assay).

As used herein, "modified Ig molecule" or "S antibody" means an immunoglobulin ("Ig") molecule that differs from a naturally-occurring Ig molecule by containing at least a portion of an additional constant domain in the constant region domain of the antibody; the additional constant domain may either be the same class or a different Ig class than the original antibody. A modified Ig molecule can be made, for example, by conventional genetic recombination using polynucleotides encoding Ig domains or portions thereof arranged in a chosen array and expressed in a cell. Alternatively, a modified Ig molecule can be synthesized using conventional techniques of polypeptide synthesis. The Ig molecule can be an IgA (which includes IgA1 and IgA2), IgM, IgG, IgD, or IgE molecule.

As used herein, "constant region domain" or "constant domain" refers to a domain within the constant portion of an Ig molecule, including $C_L$, $C_H1$, hinge, $C_H2$, $C_H3$ and $C_H4$. As used herein, a "variable region domain" or "variable domain" refers to that portion of an Ig molecule which confers specificity of the Ig for a particular antigen.

As used herein, "antigen" means a substance capable of either binding to an antigen binding region of an immunoglobulin molecule or of eliciting an immune response. As used herein, "antigen" includes, but is not limited to, antigenic determinants, haptens, and immunogens.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is 1 mM, preferably 100 nM and most preferably 10 nM.

As used herein, "vector" means a construct which is capable of delivering, and preferably expressing, one or more genes or polynucleotide sequences of interest in a host cell. Examples of vectors include, but are not limited to, viral vectors, naked DNA or RNA expression vectors, DNA or RNA expression vectors associated with cationic condensing agents, DNA or RNA expression vectors encapsulated in liposomes, and certain eucaryotic cells, such as producer cells.

As used herein, "polynucleotide" or "nucleic acid" means a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides. Unless otherwise indicated, a particular nucleic acid sequence optionally includes the complementary sequence. The polynucleotide sequence may encode variable and/or constant region domains of immunoglobulin. The term "isolated polynucleotide" as used herein shall mean a polynucleotide of genomic, cDNA, or synthetic origin or some combination thereof. By virtue of its origin the "isolated polynucleotide" (1) is not associated with all or a portion of a polynucleotide in which the "isolated polynucleotides" are found in nature, (2) is operably linked to a polynucleotide which it is not linked to in nature, or (3) does not occur in nature as part of a larger sequence.

As used herein, "pharmaceutically acceptable carrier" includes any material which, when combined with an Ig, allows the Ig to retain biological activity and is non-reactive with the subject's immune system. Examples include, but are not limited to, an y of the standard pharmaceutical carriers such as a phosphate buffered saline solution, water, emulsions such as an oil/water emulsion, and various types of wetting agents. Preferred diluents for aerosol or parenteral administration include phosphate buffered saline or normal (0.85%) saline.

As used in the appended claims, "a" means at least one, and can include a plurality.

The term "operably linked" as used herein refers to positions of in a relationship permitting them to function in the intended manner. A control sequence "operably linked" to a coding sequence is ligated in such a way that expression of the coding sequence is achieved under conditions compatible with those of the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include a promoter, ribosomal binding site, and transcription termination sequence; in eukaryotes such control sequences generally include promoters and transcription termination sequences. The term "control sequences" is intended to include, at a minimum, all components whose presence is essential for expression and processing, and can also include additional components whose presence is advantageous, leader sequences and fusion partner sequences, for example.

As used herein, the twenty conventional amino acids and their abbreviations follow conventional usage. The amino acids that make up the S antibodies of the present invention are often abbreviated. The amino acid designations can be indicated by designating the amino acid by its single letter code, its three letter code, name, or three nucleotide codon(s) as is well understood in the art (see Alberts, B., et al., *Molecular Biology of The Cell*, 3$^{rd}$ Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |

| SINGLE LETTER CODE | THREE LETTER CODE | NAME | THREE NUCLEOTIDE CODON(S) |
|---|---|---|---|
| P | Pro | Proline | CCA, CCC, CCG, CCU |
| Q | Gln | Glutamine | CAA, GAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

Stereoisomers (e.g., D-amino acids) of the twenty conventional amino acids, unnatural amino acids such as x-, x-disubstituted amino acids, N-alkylamino acids, lactic acid, and other unconventional amino acids may also be suitable components for polypeptides of the present invention. Examples of unconventional amino acids include: 4-hydroxyproline, g-carboxyglutamate, e-N,N,N-trimethyllysine, e-N-acetyllysine, 0-phosphoserine, N-acetylserine, N-formylmethionine, 3-methylhistidine, 5-hydroxylysine, s-N-methylarginine, and other similar amino acids and imino acids. In the polypeptide notation used herein, the left hand direction is the amino terminal direction and the right hand direction is the carboxy-terminal direction, in accordance with standard usage and convention.

As applied to polypeptides, the term "substantial identity" means that two peptide sequences, when optimally aligned, share at least 80% sequence identity, preferably at least 90% sequence identity, more preferably at least 95% sequence identity, and most preferably at least 99% sequence identity.

Preferably, residue positions which are not identical differ by conservative amino acid substitutions.

Conservative amino acid substitutions refer to the interchangeability of residues having similar side chains. For example: amino acids having aliphatic side chains are glycine, alanine, valine, leucine, and isoleucine; amino acids having aliphatic-hydroxyl side chains are serine and threonine; amino acids having amide-containing sidechains are asparagine and glutamine; amino acids having aromatic side chains are phenylalanine, tyrosine, and tryptophan; amino acids having basic side chains are lysine, arginine, and histidine; amino acids having sulfur-containing side chains are cysteine and methionine. Preferred-conservative amino acids substitution groups are: valine-leucine-isoleucine, phenylalanine-tyrosine,lysine-arginine, alanine-valine, glutamic-aspartic, andasparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2)basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: aliphatic-hydrox=serine, threonine; amide-containing=asparagine, glutamine; aliphatic=alanine, valine, leucine, isoleucine; aromatic=phenylalanine, tryptophan, tyrosine. For example, it is reasonable to expect that an isolated replacement of a leucine with an isoleucine or valine, an aspartate with a glutamate, a threonine with aserine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specificactivity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains.

Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. (Bowie et al. *Science* 253:164 (1991)). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2)reduce susceptibility to oxidation, (3) alter binding affinity for forming protein complexes, (4) alter binding affinities, and (4) confer or modify other physicochemical or functional properties of such analogs. Analogs can include various muteins of asequence other than the naturally occurring peptide sequence. For example, single or multiple amino acid substitutions (preferably conservative amino acid substitutions) may be made in the naturally occurring sequence (preferably in the portion of the polypeptide outside the domain(s) forming intermolecular contacts.

A conservative amino acid substitution should not substantially change the structural characteristics of the parent sequence (e.g., a replacement amino acid should not tend to break a helix that occurs in the parent sequence, or disrupt other types of secondary structures that characterize the parent sequence).

(Examples of art-recognized polypeptide secondary and S tertiary structures are described in Creighton, Ed., *Proteins, Structures and Molecular Principles* W.H. Freeman and Company, New York 1984; C. Branden and J. Tooze, eds., *Introduction to Protein Structure* Garland Publishing, New York, N.Y. 1991; Thornton et at. *Nature* 354:105 1991, which are each incorporated herein by reference.)

The term patient includes human and veterinary subjects.

B. Antibody Structure

The basic antibody structural unit comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chain constant regions are classified as $\mu$, $\delta$, $\gamma$, $\alpha$, and $\epsilon$, and define the antibody's isotype as IgM, IgD, IgG, IgA, and IgE, respectively.

Each of the gamma heavy chain constant regions contain CH1, hinge, CH2, and CH3 domains, with the hinge domain in gamma-3 being encoded by 4 different exons. (Morrison and Oi "Chimeric Ig Genes" in *Immunoglobulin Genes* pp. 259-274 Honjo et al. eds., Academic Press Limited, San Diego, Calif. 1989). Within light and heavy chains, the variable and constant regions are joined by a "J" region of about 12 or more amino acids, with the heavy chain also including a "D" region of about 10 more amino acids. (See generally: *Fundamental Immunology* Ch. 7 (Paul, W., ed., $2^{nd}$ ed. Raven Press, NY 1989) (incorporated by reference in its entirety for all purposes)). The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hyper variable regions, also called complementarity determining regions or CDRs.

The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health Bethesda, Md. 1987 and 1991; Chothia & Lesk *J. Mol. Biol.* 196:901-917 1987; Chothia et al. *Nature* 342:878-883 1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. (See, e.g., Songsivilai & Lachmann *Clin. Exp. Immunol.* 79:315-321 1990; Kostelny et al. *J. Immunol.* 148:1547-1553 1992).

Production of bispecific antibodies can be a relatively labor intensive process compared with production of conventional antibodies and yields and degree of purity are generally lower for bispecific antibodies.

Bispecific antibodies do not exist in the form of-fragments having a single binding site (e.g., Fab, Fab and Fv).

C. Antibodies of the Present Invention

The present invention is specifically related to engineering of antibody molecules so as to contain an extra immunoglobulin domain to the constant region in order modify the spatial characteristics of the antibody molecule and thus enchance the neutralization ability and stability of the molecule and the characterization of these molecules in vitro and in vivo.

In accordance with the present invention there are provided methods for the utilization of a plurality of native or modified immunoglobulin (Ig) constant domains to modify the characteristics of an antibody and thus increase the avidity and/or affinity of the molecule incorporating the same by inserting the immunoglobulin constant domain into the constant region of the antibody. In this manner, the spatial characteristics and flexibility of the two Fab domains of the antibody can be modified. Also provided in accordance with the present invention are compositions of molecules modified in accordance with the methods of the invention. Generally, methods in accordance with the the invention consist of adding at least one molecule comprising an extra immunoglobulin constant domain or a modification thereof to a molecule forming an antibody constant domain by physically linking the Ig constant domain to the constant region of the antibody.

For example, a polypeptide comprising the complete CH1 domain of an IgG constant region can be added to a constant region of an IgG2a antibody by inserting the extra CH1 domain between the CH1 and hinge domain of the normal antibody by physically linking the two domains. Physical linkage may be accomplished utilizing any conventional technique. In preferred embodiments, physical linkage of the domains is accomplished recombinantly, i.e., wherein a gene construct encoding such domains is introduced into an expression system in a manner that allows correct assembly of the molecule upon expression therefrom. The foregoing example is depicted in FIG. 1.

To construct such a modified Ig, in general, the genes encoding the extra constant domain molecule can be readily isolated and cloned into the gene encoding the constant region of the original antibody. For instance, an XbaI-ApoI restriction fragment that includes the entire CH1 domain of an IgG1 gene, along with such flanking regions as needed, can be cloned into the StuI restriction site located in the intron between the CH1 and hinge domains of an IgG2a gene, as shown in the following examples. The DNA fragments that encode the heavy chain variable regions are then cloned upstream of the modified constant region sequence to prepare a final heavy chain expression plasmid. This construct is then mixed with the light chain plasmid and transfected into a suitable cell line for expression. In this manner, the molecule depicted in FIG. 1 can be produced.

In the following examples, a sequence encoding a mouse CH1 domain was inserted downstream of the CH1 domain of a mouse IgG2a heavy chain molecule. Other preferred embodiments could include inserting a CH2 or a CH3 domain from an IgG instead of a CH1 domain. The inserted domain may also be a domain from a light chain or another Ig isotype such as IgD, in particular the CH domain that does not associate with another domain. Normally CH1 domains of heavy chains are intimately associated with a light chain constant region and this association buries hybrophobic faces on both the heavy chain and the light chain. As far as is known, the CH1 domains in the S-Abs do not associate with light chains. It is possible that the two CH1 domains of each dimer molecule associate with each other to bury the otherwise exposed hydrophobic faces. An immunoglobulin domain could be inserted between the variable region and the CH1 domain instead of between the CH1 domain and the hinge region, as long as the light chain can associate with the heavy chain.

Moreover, the inserted constant region need not be restricted to native forms of the constant regions that are present in native antibodies. Rather, the inserted constant region domain for use in accordance with the present invention can be generated through, for example, mutagenesis of constant region domains followed by screening for enhanced activity or prepared synthetically.

This invention could be practiced with Abs from other species, such as humans, non-human primates, goats, rabbits, chickens, rats, or hamsters. Other possibilities would be to insert an immunoglobulin domain from a non-Ab protein, such as CD4. The inserted sequence may not need to be an immunoglobulin domain. Other sequences may be able to confer the flexibility or spatial arrangement needed to improve Ab potency. Examples include the polypeptide linkers composed of glycine and serine residues, such as (Gly-Gly-Gly-Ser)$_3$ (SEQ. ID No. 3). However, prior to making S-cV1q and S-Rt108 Abs, cV1q was modified to include either one or three tandem copies of the flexible Gly-Gly-Gly-Ser (SEQ ID No.4) sequence to make the Abs termed cV1q-flex1 or cV1q-flex3. These Abs were expressed in cells, purified from cell supernatant, and assayed for their ability to block muTNF cytotoxicity. The results (not shown) showed that the flex versions of cV1q had the same neutralization potency as the normal cV1q Ab. It is possible that further optimization of the flexible linkers may have resulted in other versions that had increased potency.

D. Advantages

From the foregoing it will be understood by those in the art that the present invention can be utilized for a number of different purposes where added flexibility and spatial distance between the two Fab domains is desirable. For instance, the modification described here may result in:

Abs that serve as better surrogate Abs if it is desired that a surrogate Ab be functionally bivalent Abs that form desired higher-order immune complexes, especially with homopolymeric antigen a dramatic increase in the neutralization potency of an Ab and thereby decrease the amount of Ab needed for either research purposes, diagnostic purposes, or therapeutic treatments a dramatic increase in the avidity of an Ab to cells expressing the target antigen and thereby may enhance Fc-mediated immune effector mechanisms (such as Ab-dependent cellular cytotoxicity) that result from greater binding to cells; may have applicability to Abs against human antigens It will be appreciated that the present invention is also applicable to enhancing the interactions between a receptor and its ligand generally. In this respect, either receptor or ligand moieties may be modified so as to generate molecules that possess greater than one moiety that enhances the affinity, avidity, or simply the ability of receptor and ligand to interact. Stated another way, the invention, by modifying the spatial characteristics of the binding domains, provides a method to increase avidity of a molecule to its target. The end result is that the modified molecule will have a higher affinity for the target the parent molecule and consequently can be used as a competitor. In addition, because adding an extra immunoglobulin domain does not introduce foreign protein sequences the modified molecules are less likely to be immunogenic.

The ligand with higher affinity could be designed to block the function of the receptor as an antagonist or to potentially generate an extremely potent agonist.

E. Design of Modified Antibodies

As discussed above, the basic design used to prepare a preferred modified S antibody in accordance with the present invention is to incorporate an additional constant domain, such as a CH1 domain, into the constant region of an antibody. One construct in accordance with the invention is the addition of a CH1 domain to an existing antibody (as shown in FIG. 1). The antibody which is to be modified may be selected from any antibody of human, rodent or other source, and may be a chimeric, humanized, human or synthetic antibody. In one embodiment, the antibody which is to be modified may be generated through immunization of a normal or transgenic mouse. The antibody may be further modified in any of a number of ways known in the art. In general the modified antibody may be prepared by simply inserting the polynucleotide encoding the extra constant domain or other insert sequence into the plasmid encoding the constant region of the antibody and expressing the plasmid in a suitable host cell to produce the modified antibody. The insert may be made anywhere in the constant region of the immunoglobulin. In one embodiment, the insert is made downstream of the CH1 domain of the heavy chain molecule, but inserts can be made at other places in the constant region. The insert may be made directly or with a linker molecule. The nature of the insert and linker can be designed as necessary to perform the function intended, i.e. to modify the spatial characteristics and flexibilty of the binding regions of the antibody molecule. The amino acid composition and length of the insert modifying the antibody immunoglobulin molecule may be determined by testing constructs containing a variety of different sequences as known in the art.

Where a modified molecule that has certain characteristics is desired, it may be desirable or necessary to introduce certain mutations in the constant region insert so as to modify its characteristics in some way. However, where an antibody for use in humans is desired, it is desirable to make the inserts as close to human sequences as possible to reduce immunogenicity. Accordingly, it is generally desirable to introduce as few amino-acid changes to the modified molecules as possible so as to avoid generating immunogenicity.

Bispecific, heterospecific, heteroconjugate or similar monoclonal, humanized antibodies that have binding specificities for at least two different antigens can also be used. In such a case, one of the binding specificities may be designated for one antigen and the other one is for any other antigen. Methods for making bispecific antibodies are known in the art. Traditionally, the recombinant production of bispecific antibodies is based on the co-expression of two immunoglobulin heavy chain/light chain pairs, where the two heavy chains have different specificities (Milstein and Cuello, *Nature* 305:537 1983). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, (e.g., WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 1991; Suresh et al., *Methods in Enzymology* 121:210 1986, each entirely incorporated herein by reference).

In the following examples, the modified Ab was prepared by using recombinant DNA methods to add the DNA sequence encoding the complete CH1 domain of the mouse IgG1 constant region into the gene encoding the mouse IgG2a constant region of the antibodies cV1q and rRt108. The extra CH1 domain was inserted between the CH1 and hinge domains of the normal Abs (FIG. 2). Specifically, an XbaI-ApoI restriction fragment that included the entire CH1 domain of the mouse IgG1 gene and some flanking intron sequences was cloned into the StuI restriction site located in the intron between the CH1 and hinge domains of the mouse IgG2a gene. The DNA fragments that encoded either the cV1q or Rt108 heavy chain variable regions were then cloned upstream of the modified constant region sequence to prepare a final heavy chain expression plasmid. The heavy chain plasmid was mixed with the same light chain plasmid previously used to express the normal Abs and introduced together into mouse myeloma cells by electroporation. Transfected cells that secreted either S-cV1q or S-rRt108 were identified by assaying cell supernatant for mouse IgG by conventional ELISA techniques. Producing cell lines were scaled up and then the S-Abs were purified from cell supernatant by conventional protein A chomatography.

Passage of the purified S-Abs through an SDS-containing polyacrylamide gel confirmed that their heavy chains were of higher molecular weight (approximately 15 kDa higher, as expected) than the corresponding heavy chains of the normal Abs (FIG. 3). The light chains of the S-Abs and normal Abs were of the same molecular weight, as expected. The sequences for the modified antibody compared to the unmodified murine antibody from which it was derived, are shown in FIG. 2.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR4, CDR5 and CDR6) or variant of at least one light chain variable region, framework regions and a light chain and heavy chain constant region which has been modified as described. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

Preferably, the S antibody or ligand-binding portion or variant thereof binds at least one protein ligand or receptor, and thereby provides at least one biological activity of the corresponding protein or a fragment thereof. Different therapeutically or diagnostically significant proteins are well known in the art and suitable assays or biological activities of such proteins are also well known in the art. S antibodies that bind any number of biologically active proteins may be used in conjunction with the present invention. Of particular interest are S antibodies that bind to, and thus modulate the activity of TNF, leptin, any of the interleukins (IL-1 through IL-23, etc.), and proteins involved in complement activation (e.g., C3b). Targeting proteins that are differentially expressed in certain disease states are also of interest, including proteins expressed on tumors and the like. All of these classes of ligands may be discovered by methods described in the references cited in this specification and other references. A particularly preferred group of S antibodies are those that bind to cytokine receptors. Cytokines have recently been classified according to their receptor code (see Inglot 1997, *Archivum Immunologiae Therapiae Experimentalis* 45: 353-7, which is hereby incorporated entirely by reference).

Modified S antibodies of the invention that comprise a modified constant region can be prepared using suitable methods, such as phage display (Katsube, Y., et al., *Int J Mol. Med,* 1(5):863-868 1998) or methods that employ transgenic animals, as known in the art and/or as described herein. For example, the antibody, or a specified portion or variant thereof, can be expressed using the encoding nucleic acid or portion thereof in a suitable host cell.

The invention also relates to modified antibodies that are substantially the same as an amino acid sequence described herein. Preferably, such antibodies or antigen-binding fragments and antibodies comprising such chains or CDRs can bind the desired antigen with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/ hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

An S antibody of the present invention can include one or more amino acid substitutions, deletions or additions, either from natural mutation or human manipulation, from the parent antibody from which it was derived.

Amino acids in an S antibody of the present invention that are essential for function can be identified by methods known in the art, such as site-directed mutagenesis or alanine-scanning mutagenesis (e.g., Ausubel, supra, Chapters 8, 15; Cunningham and Wells, *Science* 244:1081-1085 1989). The latter procedure introduces single alanine mutations at every residue in the molecule. The resulting mutant molecules are then tested for biological activity, such as, but not limited to at least one S neutralizing activity. Sites that are critical for antibody binding can also be identified by structural analysis such as crystallization, nuclear magnetic resonance or photoaffinity labeling (Smith, et al., *J. Mol. Biol.* 224:899-904 1992; de Vos, et al., *Science* 255:306-312 1992).

S antibodies of the present invention can include, but are not limited to, at least one portion, sequence or combination selected from at least 5 of the contiguous amino acids of at least one of SEQ ID NOS:1

An S antibody can further optionally comprise a polypeptide of at least one of 70-100% of the contiguous amino acids of at least one of SEQ ID NOS:1

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:1 For example, the amino acid sequence of a light chain variable region can be compared with the light chain sequence of SEQ ID NO:1, or the amino acid sequence of a heavy chain CDR3 can be compared with the heavy chain CDR3 sequence of SEQ ID NO:1. Preferably, 70-100% amino acid identity (i.e., 90, 91, 92, 93, 94, 95, 96, 97, 98, 99, 100 or any range or value therein) is determined using a suitable computer algorithm, as known in the art.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibodies. Methods of assaying and quantifying measures of enzymatic activity and substrate specificity are well known to those of skill in the art.

In another aspect, the modified S antibody, as described herein, may be further modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cisα α9-octadecanoate ($C_{18}$, oleate), all cisα5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see e.g., Hermanson, G. T., *Bioconjugate Techniques*, Academic Press San Diego, Calif. 1996). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See e.g., Thompson, et al., WO 92/16221; the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 1992; Werlen et al., *Bioconjugate Chem.*, 5:411-417 1994; Kumaran et al., *Protein Sci.* 6(10):2233-2241 1997; Itoh et al., *Bioorg. Chem.*, 24(1): 59-68 1996; Capellas et al., *Biotechnol. Bioeng.*, 56(4):456-463 1997; and the methods described in Hermanson, G. T., *Bioconjugate Techniques*, Academic Press San Diego, Calif. 1996)

F. Preparation of Modified S Antibodies

Human genes which encode the constant (C) regions of the chimeric antibodies, fragments and regions of the present invention can be derived from a human fetal liver library by known methods. Human C region genes can be derived from any human cell including those which express and produce human immunoglobulins. The human $C_H$ region can be derived from any of the known classes or isotypes of human H chains, including γ, μ, α, δ, ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from γ1 (IgG1). The human $C_L$ region can be derived from either human L chain isotype, κ or λ, preferably κ.

Genes encoding human immunoglobulin C regions are obtained from human cells by standard cloning techniques (Sambrook, et al. *Molecular Cloning: A Laboratory Manual*, $2^{nd}$ Edition, Cold Spring Harbor Press, Cold Spring Harbor, N.Y. 1989; Ausubel et al, eds. *Current Protocols in Molecular Biology* 1987-1993). Human C region genes are readily available from known clones containing genes representing the two classes of L chains, the five classses of H chains and subclasses thereof. Chimeric antibody fragments, such as F(ab₁)₂ and Fab, can be prepared by designing a chimeric H chain gene which is appropriately truncated. For example, a chimeric gene encoding an H chain portion of an F(ab¹)₂ fragment would include DNA sequenes encoding the CH1 domain and hinge region of the H chain, followed by a translational stop codon to yield the truncated molecule.

Generally, the murine, human or murine and chimeric antibodies, fragments and regions of the present invention are produced by cloning DNA segments encoding the H and L chain antigen-binding regions of a specific antibody, and joining these DNA segments to DNA segments enclodingC$_H$ and $C_L$ regions, respectively, to produce murine, human or chimeric immunoglobulin-encoding genes.

Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region containing the inserted sequence.

The sequences of the variable, constant or insert sequence, may be modified by insertions, substitutions and deletions to the extent that the chimeric antibody maintains the ability to bind to and inhibit the antigen of interest. The ordinarily skilled artisan can ascertain the maintenance of this activity by performing the functional assays applicable.

The S antibody of the present invention can be optionally produced by a cell line, a mixed cell line, an immortalized cell or clonal population of immortalized cells, as well known in the art. (See, e.g., Ausubel, et al., ed., *Current Protocols in Molecular Biology*, John Wiley & Sons, Inc., NY, N.Y. 1987-2001; Sambrook, et al., *Molecular Cloning: A Laboratory Manual*, $2^{nd}$ Edition, Cold Spring Harbor, N.Y. 1989; Harlow and Lane, *antibodies, a Laboratory Manual*, Cold Spring Harbor, N.Y. 1989; Colligan, et al., eds., *Current Protocols in Immunology*, John Wiley & Sons, Inc., NY 1994-2001; Colligan et al., *Current Protocols in Protein Science*, John Wiley & Sons, NY, N.Y. 1997-2001, each entirely incorporated herein by reference.)

In one approach, a hybridoma is produced by fusing a suitable immortal cell line (e.g., a myeloma cell line such as, but not limited to, Sp2/0, Sp2/0-AG14, NS/O, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. (See, e.g., www.atcc.org, www.lifetech.com.), and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. (See, e.g., Ausubel, supra, and *Colligan, Immunology*, supra, chapter 2, entirely incorporated herein by reference.)

Any other suitable host cell can also be used for expressing heterologous or endogenous nucleic acid encoding an antibody, specified fragment or variant thereof, of the present invention. The fused (hybridomas) or recombinant cells can be isolated using selective culture conditions or other suitable known methods, and cloned by limiting dilution, cell sorting, or other known methods. Cells which produce antibodies with the desired specificity can be selected by a suitable assay (e.g., ELISA).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., in a number of public databases such as the NCBI database of the National Institute of Health or publications such as Kabat et al., Sequences of Proteins of Immunological Interest, U.S. Dept. Health (1983).

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in: (Winter, Jones et al., Nature 321:522 1986; Riechmann et al., Nature 332:323 1988; Verhoeyen et al., Science 239:1534 1988; Sims et al., J. Immunol. 151: 2296 1993; Chothia and Lesk, J. Mol. Biol. 196:901 1987; Carter et al., Proc. Natl. Acad. Sci. U.S.A. 89:4285 1992; Presta et al., J. Immunol. 151:2623 1993; U.S. Pat. Nos.: 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.)

Antibodies of the present invention can also be prepared using at least one S antibody encoding nucleic acid to provide transgenic animals or mammals, such as goats, cows, horses, sheep, and the like, that produce such antibodies in their milk. Such animals can be provided using known methods. (See, e.g., but not limited to, U.S. Pat. Nos.: 5,827,690; 5,849,992; 4,873,316; 5,849,992; 5,994,616, 5,565,362; 5,304,489, and the like, each of which is entirely incorporated herein by reference.)

Antibodies of the present invention can additionally be prepared using at least one S antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. (See, e.g., Cramer et al., Curr. Top. Microbol. Immunol. 240:95-118 1999) and references cited therein. Also, transgenic maize has been used to express mammalian proteins at commercial production levels, with biological activities equivalent to those produced in other recombinant systems or purified from natural sources. (See, e.g., Hood et al., Adv. Exp. Med. Biol. 464:127-147 1999 and references cited therein.) Antibodies have also been produced in large amounts from transgenic plant seeds including antibody fragments, such as single chain antibodies (scFv's), including tobacco seeds and potato tubers. (See, e.g., Conrad et al., Plant Mol. Biol. 38:101-109 1998 and reference cited therein.) Thus, antibodies of the present invention can also be produced using transgenic plants, according to know methods. (See also, e.g., Fischer et al., Biotechnol. Appl. Biochem. 30:99-108 October, 1999: Ma et al., Trends Biotechnol. 13:522-7 199; Ma et al., Plant Physiol. 109:341-6 1995; Whitelam et al., Biochem. Soc. Trans. 22:940-944 1994; and references cited therein; each of the above references is entirely incorporated herein by reference.)

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press NY, N.Y. 1984; Kuby, Janis Immunology, W. H. Freeman and Company NY, N.Y. 1992; and methods described herein.) The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

G. Nucleic Acid Molecules

Using the information provided herein, a nucleic acid molecule of the present invention encoding at least one S antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, at least one specified portion of at least one CDR, as CDR 1, CDR2 and/or CDR3 of at least one heavy chain or light chain nucleic acid molecules comprising the coding sequence for an S antibody and nucleic acid molecules which comprise a nucleotide sequence substantially different from those described above but which, due to the degeneracy of the genetic code, still encode at least one such S antibody as described herein and/or as known in the art. Of course, the genetic code is well known in the art. Thus, it would be routine for one skilled in the art to generate such degenerate nucleic acid variants that code for specific anti-S antibodies of the present invention. (See, e.g., Ausubel, et al., supra), and such nucleic acid variants are included in the present invention..

As indicated herein, nucleic acid molecules of the present invention which comprise a nucleic acid encoding an anti-S antibody can include, but are not limited to, those encoding the amino acid sequence of an antibody fragment by itself, the coding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

H. Polynucleotides which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. (See, e.g., Ausubel, supra; Colligan, supra; each entirely incorporated herein by reference.)

I. Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expressing a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

J. Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

K. Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization could be conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (see, e.g., Ausubel, supra; Sambrook, supra; U.S. Pat. No. 5,130,238 to Malek, et al, with the tradename NASBA; the entire contents of which references are incorporated herein by reference).

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. (Examples of techniques sufficient to direct persons of skill through in vitro amplification methods are found in: Berger, supra; Sambrook, supra; Ausubel, supra; Mullis, et al., U.S. Pat. No. 4,683,202 1987; Innis, et al., PCR *Protocols A Guide to Methods and Applications*, Eds., Academic Press Inc., San Diego, Calif. 1990.) Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

L. Synthetic Methods for Constructing Nucleic Acids

The isolated nucleic acids of the present invention can also be prepared by direct chemical synthesis using known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

M. Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

N. Vectors and Host Cells

The present invention also relates to vectors that include isolated nucleic acid molecules of the present invention, host cells that are genetically engineered with the recombinant vectors, and the production of at least one anti-S antibody by recombinant techniques, as is well known in the art. ( See, e.g., Sambrook, et al., supra; Ausubel, et al., supra, each entirely incorporated herein by reference.)

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. (Such methods are described in the art: Sambrook, supra, Chapters 1-4 and 16-18; Ausubel, supra, Chapters 1, 9, 13, 15, 16.)

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. (Such methods are described in many standard laboratory manuals: Sambrook, supra; Chapters 17.29-17.42 and 18.1-18.74; Ausubel, supra, Chapters 16, 17 and 18.)

Those of ordinary skill in the art are knowledgeable in the numerous expression systems available for expression of a nucleic acid encoding a protein of the present invention. Alternatively, nucleic acids of the present invention can be expressed in a host cell by turning on (by manipulation) in a host cell that contains endogenous DNA encoding an antibody of the present invention. (Such methods are well known in the art, e.g., as described in U.S. Pat. Nos. 5,580,734, 5,641,670, 5,733,746, and 5,733,761, entirely incorporated herein by reference.)

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra.) Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 1983). Additionally, gene sequences to control replication in the host cell can be incorporated into the vector, as known in the art.

O. Cloning and Expression of S Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 1991; Bebbington, et al., Bio/Technology 10:169-175 1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 1985) plus a fragment of the CMV-enhancer (Boshart, et al., Cell 41:521-530 1985). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

P. Cloning and Expression in CHO Cells

The vector pC4 is used for the expression of the S antibody. Plasmid pC4 is a derivative of the plasmid pSV2-dhfr (ATCC Accession No. 37146). The plasmid contains the mouse DHFR gene under control of the SV40 early promoter. Chinese hamster ovary or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 1978; J. L. Hamlin and C. Ma, Biochem. et Biophys. Acta 1097:107-143 1990; and M. J. Page and M. A. Sydenham, Biotechnology 9:64-68 1991). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 1985) plus a fragment isolated from the enhancer of the immediate early gene of human cytomegalovirus (CMV) (Boshart, et al., Cell 41:521-530 1985). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the S antibody in a regulated way in mammalian cells (M. Gossen, and H. Bujard, Proc. Natl. Acad. Sci. USA 89: 5547-5551 1992). For the polyadenylation of the mRNA other signals, e.g., from the human growth hormone or globin, genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete S antibody is used, e.g., as presented in SEQ ID NOS: 7, and 8, corresponding to HC and LC variable regions of a S antibody of the present invention, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 □g of the plasmid pSV2-neo using lipofectin. The plasmid pSV2neo contains a dominant selectable marker, the neo-gene from Tn5 encoding an enzyme that confers resistance to a group of antibiotics including G418. The cells are seeded in α minus MEM supplemented with 1 μg/ml G418. After 2 days, the cells are trypsinized and seeded in hybridoma cloning plates (Greiner, Germany) in α minus MEM supplemented with 10, 25, or 50 ng/ml of methotrexate plus 1 μg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

Q. Purification of an Antibody

An S antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. (See, e.g., Colligan, *Current Protocols in Immunology*, or *Current Protocols in Protein Science*, John Wiley & Sons, NY, N.Y., 1997-2001, Chapters 1, 4, 6, 8, 9, 10, each entirely incorporated herein by reference.)

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals (Sambrook, supra, Sections 17.37-17.42; Ausubel, supra, Chapters 10, 12, 13, 16, 18 and 20, Colligan, *Protein Science*, supra, Chapters 12-14, all entirely incorporated herein by reference.)

R. Utility

The isolated nucleic acids of the present invention can be used for production of at least one S antibody or specified variant thereof, which can be used to measure an effect in a cell, tissue, organ or animal (including mammals and humans), to diagnose, monitor, modulate, treat, alleviate, help prevent the incidence of, or reduce the symptoms of, at least one condition, selected from, but not limited to, at least one of an immune disorder or disease, a cardiovascular disorder or disease, an infectious, malignant, and/or neurologic disorder or disease, an allergic disorder or disease; a skin disorder or disease; a hematological disorder or disease, and/or or a pulmonary disorder or disease, or other known or specified condition.

Such a method can comprise administering an effective amount of a composition or a pharmaceutical composition comprising at least one S antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous adminstration, or any effective range or value therein, as done and determined using known methods, as described herein or known in the relevant arts.

S. S Antibody Compositions

The present invention also provides at least one S antibody composition comprising at least one, at least two, at least three, at least four, at least five, at least six or more S antibodies thereof, as described herein and/or as known in the art that are provided in a non-naturally occurring composition, mixture or form. Such compositions comprise non-naturally occurring compositions comprising at least one S antibodies of the invention in combination with a pharmaceutically acceptable carrier. Such S antibody compositions can include anywhere from 40-99% of the S antibody of the invention. Such composition percentages are by weight, volume, concentration, molarity, or molality as liquid or dry solutions, mixtures, suspension, emulsions or colloids, as known in the art or as described herein.

S antibody or specified portion or variant compositions of the present invention can further comprise at least one of any suitable auxiliary, such as, but not limited to, diluent, binder, stabilizer, buffers, salts, lipophilic solvents, preservative, adjuvant or the like.

Pharmaceutically acceptable auxiliaries are preferred. Non-limiting examples of, and methods of preparing such sterile solutions are well known in the art; (Gennaro, Ed., *Remington's Pharmaceutical Sciences*, 18$^{th}$ Edition, Mack Publishing Co. Easton, Pa. 1990.) Pharmaceutically acceptable carriers can be routinely selected that are suitable for the mode of administration, solubility and/or stability of the S antibody composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/S antibody or specified portion or variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

S antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, the S antibody or specified portion or variant compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the S antibody compositions according to the invention are known in the art, (e.g., as listed in *Remington: The Science & Practice of Pharmacy*, 19th ed., Williams & Williams, 1995; *Physician's Desk Reference*, 52nd ed., Medical Economics, Montvale, N.J. 1998 the disclosures of which are entirely incorporated herein by reference.) Preferrred carrier or excipient materials are carbohydrates (e.g., saccharides and alditols) and buffers (e.g., citrate) or polymeric agents.

T. Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-S antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein.

Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one S antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one S antibody, and a second vial comprising an aqueous diluent of prescribed buffer or preservative, wherein said packaging material comprises a label that instructs a patient to reconstitute the at least one anti-S antibody in the aqueous diluent to form a solution that can be held over a period of twenty-four hours or greater.

The range of at least one S antibody in the product of the present invention includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), TWEEN 40 (polyoxyethylene (20) sorbitan monopalmitate), TWEEN 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-S antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-S antibody and preservative in an aqueous diluent is carried out using conventional dissolution and mixing procedures. To prepare a suitable formulation, for example, a measured amount of at least one anti-S antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-S antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one S antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-S antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one S antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www-.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-S antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one S antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-S antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one S antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

U. Therapeutic Applications

The present invention also provides a method for modulating or treating a disease, in a cell, tissue, organ, animal, or patient, as known in the art or as described herein, using at least one S antibody of the present invention.

The present invention also provides a method for modulating or treating at least one disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, asteoarthritis, inflammatory bowel disease, ulverative colitis, systemic lupus erythomatosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, sleep apnea, obesity, heart failure, sinusitis, inflammatory bowel disease, and the like. (See, e.g., the Merck Manual, 12$^{th}$-17$^{th}$ Editions, Merck & Company, Rahway, N.J. 1972, 1977, 1982, 1987, 1992, 1999; Wells et al., eds., Pharmacotherapy Handbook, 2$^{nd}$ Edition, Appleton and Lange, Stamford, Conn. 1998, 2000 each entirely incorporated by reference.)

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A,B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, lyme disease, influenza a, epstein-barr virus, vital-associated hemaphagocytic syndrome, vital encephalitis/aseptic meningitis, and the like.

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like. Such a method can optionally be used in combination with, by administering before, concurrently or after administration of such S antibody, radiation therapy, an anti-angiogenic agent, a chemotherapeutic agent, a farnesyl transferase inhibitor or the like.

In particular, the present invention provides a method for modulating or treating autoimmune diseases such as rheumatoid arthritis, systemic lupus erythematosus, and autoimmune insulin dependent diabetes; the treatment of bacterial infections; the treatment of septic shock due to bacterial infections; the treatment of viral infections; the treatment of cancers such as multiple myeloma; the suppression of cancer metastasis; the amelioration of cancer cachexia; and the treatment of inflammatory diseases such as mesangial proliferative glomerulonephritis, by the administration of the antibody of the invention. Such a method can optionally comprise administering an effective amount of at least one composition or pharmaceutical composition comprising at least one S antibody to a cell, tissue, organ, animal or patient in need of such modulation, treatment or therapy.

Any method of the present invention can comprise administering an effective amount of a composition or pharmaceutical composition comprising at least one S antibody to a cell, tissue, organ, animal or patient in need of such modulation, treatment or therapy. Such a method can optionally further comprise co-administration or combination therapy for treating such immune diseases or malignant diseases, wherein the administering of said at least one S antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an IL-18 antibody or fragment, small molecule IL-18 antagonist or IL-18 receptor binding protein, an IL-1 antibody (including both IL-1 alpha and IL-1 beta) or fragment, a soluble IL-1 receptor antagonist, an antirheumatic (e.g., methotrexate, auranofin, aurothioglucose, azathioprine, etanercept, gold sodium thiomalate, hydroxychloroquine sulfate, leflunomide, sulfasalazine, radiation therapy, an anti-angiogenic agent, a chemotherapeutic agent, Thalidomide), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. (See, e.g., Wells et al., eds., *Pharmacotherapy Handbook*, 2$^{nd}$ Edition, Appleton and Lange, Stamford, Conn. 2000; PDR Pharmacopoeia, *Tarascon Pocket Pharmacopoeia* 2000, *Deluxe Edition*, Tarascon Publishing, Loma Linda, Calif. 2000, each of which references are entirely incorporated herein by reference.)

Typically, treatment of pathologic conditions is effected by administering an effective amount or dosage of at least one anti-S antibody composition that total, on average, a range from at least about 0.01 to 500 milligrams of at least one anti-S antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 μg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6,, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of *Remington's Pharmaceutical Sciences*, A. Osol, a standard reference text in this field.

V. Alternative Administration

Many known and developed modes of can be used according to the present invention for administering pharmaceutically effective amounts of at least one anti-S antibody according to the present invention. While pulmonary administration is used in the following description, other modes of administration can be used according to the present invention with suitable results.

S antibodies of the present invention can be delivered in a carrier, as a solution, emulsion, colloid, or suspension, or as a dry powder, using any of a variety of devices and methods suitable for administration by inhalation or other modes described here within or known in the art.

W. Parenteral Formulations and Administration

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aquous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

X. Alternative Delivery

The invention further relates to the administration of at least one anti-S antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-S antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al., *Drug Permeation Enhancement*; Hsieh, D. S., Eds., pp. 59-90, Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Y. Pulmonary/Nasal Administration

For pulmonary administration, preferably at least one anti-S antibody composition is delivered in a particle size effective for reaching the lower airways of the lung or sinuses. According to the invention, at least one anti-S antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-S antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 μm, preferably about 1-5 μm, for good respirability.

Z. Administration of S Antibody Compositions as a Spray

A spray including S antibody composition protein can be produced by forcing a suspension or solution of at least one anti-S antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-S antibody composition protein delivered by a sprayer have a particle size less than about 10 µm, preferably in the range of about 1 µm to about 5 µm, and most preferably about 2 µm to about 3 µm.

Formulations of at least one anti-S antibody composition protein suitable for use with a sprayer typically include antibody composition protein in an aqueous solution at a concentration of about 0.1 mg to about 100 mg of at least one anti-S antibody composition protein per ml of solution or mg/gm, or any range or value therein, e.g., but not limited to, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as S antibodies, or specified portions or variants, can also be included in the formulation.

AA. Administration of S Antibody Compositions by a Nebulizer

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 µm, preferably in the range of about 1 µm to about 5 µm, and most preferably about 2 µm to about 3 µm.

Formulations of at least one anti-S antibody suitable for use with a nebulizer, either jet or ultrasonic, typically include a concentration of about 0.1 mg to about 100 mg of at least one anti-S antibody protein per ml of solution. The formulation can include agents such as an excipient, a buffer, an isotonicity agent, a preservative, a surfactant, and, preferably, zinc. The formulation can also include an excipient or agent for stabilization of the at least one anti-S antibody composition protein, such as a buffer, a reducing agent, a bulk protein, or a carbohydrate. Bulk proteins useful in formulating at least one anti-S antibody composition proteins include albumin, protamine, or the like. Typical carbohydrates useful in formulating at least one anti-S antibody include sucrose, mannitol, lactose, trehalose, glucose, or the like. The at least one anti-S antibody formulation can also include a surfactant, which can reduce or prevent surface-induced aggregation of the at least one anti-S antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

AB. Administration of S Antibody Compositions by a Metered Dose Inhaler

In a metered dose inhaler (MDI), a propellant, at least one anti-S antibody, and any excipients or other additives are contained in a canister as a mixture including a liquefied compressed gas. Actuation of the metering valve releases the mixture as an aerosol, preferably containing particles in the size range of less than about 10 µm, preferably about 1 µm to about 5 µm, and most preferably about 2 µm to about 3 µm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-S antibody for use with a metered-dose inhaler device will generally include a finely divided powder containing at least one anti-S antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-S antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one anti-S antibody compositions via devices not described herein.

AC. Oral Formulations and Administration

Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain another type(s) of additive, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat. No. 5,879,681 and U.S. Pat. No. 5,871,753 are used to deliver biologically active agents orally are known in the art.

AD. Mucosal Formulations and Administration

For absorption through mucosal surfaces, compositions and methods of administering at least one anti-S antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

AE. Transdermal Formulations and Administration

For transdermal administration, the at least one anti-S antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

AF. Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770, 222; *Sustained and Controlled Release Drug Delivery Systems*, J. R. Robinson ed., Marcel Dekker, Inc., NY, 1978).

Having generally described the invention, the same will be more readily understood by reference to the following examples, which are provided by way of illustration and are not intended as limiting.

EXAMPLE 1

Preparation of Modified Anti-Mouse TNF Antibody

The modified Ab was prepared by using recombinant DNA methods to add DNA sequence encoding the complete CH1 domain of the mouse IgG1 constant region into the gene encoding the mouse IgG2a constant region of mouse anti-TNF antibody (cV1q) and rat anti-TNF antibody (rRt108). The extra CH1 domain was inserted between the CH1 and hinge domains of the normal Abs (FIG. 2). Specifically, an XbaI-ApoI restriction fragment that included the entire CH1 domain of the mouse IgG1 gene and some flanking intron sequences was cloned into the StuI restriction site located in the intron between the CH1 and hinge domains of the mouse IgG2a gene. The DNA fragments that encoded either the cV1q or Rt108 heavy chain variable regions were then cloned upstream of the modified constant region sequence to prepare a final heavy chain expression plasmid. The heavy chain plasmid was mixed with the same light chain plasmid previously used to express the normal Abs and introduced together into mouse myeloma cells by electroporation. Transfected cells that secreted either S-cV1q or S-rRt108 were identified by assaying cell supernatant for mouse IgG by conventional ELISA techniques. Producing cell lines were scaled up and then the S-Abs were purified from cell supernatant by conventional protein A chomatography.

Passage of the purified S-Abs through an SDS-containing polyacrylamide gel confirmed that their heavy chains were of higher molecular weight (approximately 15 kDa, as expected) than the corresponding heavy chains of the normal Abs (FIG. 3). The light chains of the S-Abs and normal Abs were of the same molecular weight, as expected.

Cell-based functional assays showed that S-cV1q was approximately 200-fold more potent than cV1q in neutralizing muTNF (FIG. 4A) and that S-rRt108 was approximately 20-fold more potent than rRt108 in neutralizing rat TNF (FIG. 4B). These results indicated that the desired increase in neutralization potency could indeed be realized by addition of an extra immunoglobulin domain to the constant region. Interestingly, a 200-fold difference in TNF-neutralizing potency was also was observed in comparisons between cV1q and the original V1q Ab (the IgD version believed to be functionally bivalent) and between cV1q and cV1q cross-linked with polyclonal goat anti-muFc Ab.

Binding studies in which normal or S-Abs were bound to TNF immobilized on EIA plates and then incubated with solution-phase $^{125}$I-labeled TNF supported the expectation that the S-Abs had a greater capacity than the normal Abs to bind two TNF molecules simultaneously (FIG. 5). Interestingly, the fold difference between cV1q and S-cV1q is greater than the fold difference between rRt108 and S-rRt108, consistent with the greater difference between cV1q and S-cV1q in the WEHI assay. These data indicate that S-rRt108, and especially S-cV1q, probably form higher-order complexes whereas their normal Ab counterparts do not (FIG. 6).

The pharmacokinetic profiles of cV1q and S-cV1q were compared in mice and the pharmacokinetic profile of Rt108 and S-Rt108 were compared in rats. The results (Table 2) showed that the serum half-life for S-cV1q in mice was approximately half as long as the half-life for cV1q. In contrast, the half-life of S-Rt108 was just as long as the half-life for Rt108. Although S-cV1q cleared from circulation faster than cV1q, a 68 hr half-life is reasonable for a rat/mouse chimeric Ab and serves to validate the use of these Abs as surrogates in rodents.

TABLE 2

Pharmacokinetic Analyses of cV1q and S-cV1q in Mice and of Rt108 and S-Rt108 in Rats

| Antibody | Serum half-life |
|---|---|
| cV1q | 5.2 days |
| S-cV1q | 2.8 days |
| Rt108 | 1.7 days |
| S-Rt108 | 1.8 days |

Mice were injected with either $^{125}$I-labeled cV1q or S-cV1q and rats were injected with either $^{125}$I-labeled Rt108 or S-Rt108 as a single intravenous bolus.

What is claimed is:

1. A modified IgA, IgM, IgG, IgD, or IgE immunoglobulin antibody molecule having an antigen binding domain and a constant region, wherein the constant region has a complete $C_H1$ constant region immunoglobulin domain inserted between the $C_H1$ and hinge domain of the constant region of the immunoglobulin molecule, wherein the modified immunoglobulin antibody molecule binds antigen.

2. The modified immunoglobulin molecule of claim 1, wherein the immunoglobulin molecule is IgG1.

3. The modified immunoglobulin molecule of claim 2, wherein the inserted constant region immunoglobulin (Ig) domain comprises a $C_H1$ domain of an IgG2a immunoglobulin.

4. A pharmaceutical composition comprising the modified immunoglobulin molecule of claim 1 and a pharmaceutically acceptable carrier.

5. A composition according to claim 4, further comprising at least one compound or protein selected from a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, a diabetes related agent, a mineral, a thyroid agent, a vitamin, a calcium related hormone, an antidiarrheal, an antitussive, an antiemetic, an antiulcer, a laxative, an anticoagulant, an erythropoietin, a filgrastim, a sargramostim, an immunization, an immunoglobulin, an immunosuppressant, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha, a cytokine, and a cytokine antagonist.

6. A formulation comprising at least one modified immunoglobulin according to claim 1, and at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, in an aqueous diluent.

7. A formulation of claim 6, wherein the concentration of modified immunoglobulin is about 0.1 mg/ml to about 100 mg/ml.

8. A formulation of claim 6, further comprising an isotonicity agent.

9. A formulation of claim 6, further comprising a physiologically acceptable buffer.

10. A formulation comprising at least one modified immunoglobulin according to claim 1 in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent.

11. A formulation of claim 10, further comprising an isotonicity agent.

12. A formulation of claim 10, further comprising a physiologically acceptable buffer.

13. The modified immunoglobulin molecule of claim 2, wherein the inserted constant region immunoglobulin (Ig) domain comprises a $C_H1$ domain of an IgG1 immunoglobulin.

* * * * *

SEQUENCE LISTING

<160> NUMBER OF SEQ ID NOS: 2

<210> SEQ ID NO 1
<211> LENGTH: 329
<212> TYPE: PRT
<213> ORGANISM: murine

<400> SEQUENCE: 1

```
Lys Thr Thr Ala Pro Ser Val Tyr Pro Leu Ala Pro Val Cys Gly Asp
1               5                   10                  15

Thr Thr Gly Ser Ser Val Thr Leu Gly Cys Leu Val Lys Gly Tyr Phe
            20                  25                  30

Pro Glu Pro Val Thr Leu Thr Trp Asn Ser Gly Ser Leu Ser Ser Gly
        35                  40                  45

Val His Thr Phe Pro Ala Val Leu Gln Ser Asp Leu Tyr Thr Leu Ser
    50                  55                  60

Ser Ser Val Thr Val Thr Ser Ser Thr Trp Pro Ser Gln Ser Ile Thr
65                  70                  75                  80

Cys Asn Val Ala His Pro Ala Ser Ser Thr Lys Val Asp Lys Lys Ile
                85                  90                  95

Ala Pro Arg Gly Pro Thr Ile Lys Pro Cys Pro Pro Cys Lys Cys Pro
            100                 105                 110

Ala Pro Asn Leu Leu Gly Gly Pro Ser Val Phe Ile Phe Pro Pro Lys
        115                 120                 125

Ile Lys Asp Val Leu Met Ile Ser Leu Ser Pro Ile Val Thr Cys Val
    130                 135                 140

Val Val Asp Val Ser Glu Asp Asp Pro Asp Val Gln Ile Ser Trp Phe
145                 150                 155                 160

Val Asn Asn Val Glu Val His Thr Ala Gln Thr Gln Thr His Arg Glu
                165                 170                 175

Asp Tyr Asn Ser Thr Leu Arg Val Val Ser Ala Leu Pro Ile Gln His
            180                 185                 190
```

-continued

```
Gln Asp Trp Met Ser Gly Lys Glu Phe Lys Cys Lys Val Asn Asn Lys
            195                 200                 205

Asp Leu Pro Ala Pro Ile Glu Arg Thr Ile Ser Lys Pro Lys Gly Ser
    210                 215                 220

Val Arg Ala Pro Gln Val Tyr Val Leu Pro Pro Glu Glu Glu Met
225                 230                 235                 240

Thr Lys Lys Gln Val Thr Leu Thr Cys Met Val Thr Asp Phe Met Pro
                245                 250                 255

Glu Asp Ile Tyr Val Glu Trp Thr Asn Asn Gly Lys Thr Glu Leu Asn
            260                 265                 270

Tyr Lys Asn Thr Glu Pro Val Leu Asp Ser Asp Gly Ser Tyr Phe Met
        275                 280                 285

Tyr Ser Lys Leu Arg Val Glu Lys Lys Asn Trp Val Glu Arg Asn Ser
    290                 295                 300

Tyr Ser Cys Ser Val Val His Glu Gly Leu His Asn His His Thr Thr
305                 310                 315                 320

Lys Ser Phe Ser Arg Thr Pro Gly Lys
                325

<210> SEQ ID NO 2
<211> LENGTH: 426
<212> TYPE: PRT
<213> ORGANISM: murine

<400> SEQUENCE: 2

Lys Thr Thr Ala Pro Ser Val Tyr Pro Leu Ala Pro Val Cys Gly Asp
1               5                   10                  15

Thr Thr Gly Ser Ser Val Thr Leu Gly Cys Leu Val Lys Gly Tyr Phe
            20                  25                  30

Pro Glu Pro Val Thr Leu Thr Trp Asn Ser Gly Ser Leu Ser Ser Gly
        35                  40                  45

Val His Thr Phe Pro Ala Val Leu Gln Ser Asp Leu Tyr Thr Leu Ser
    50                  55                  60

Ser Ser Val Thr Val Thr Ser Ser Thr Trp Pro Ser Gln Ser Ile Thr
65                  70                  75                  80

Cys Asn Val Ala His Pro Ala Ser Ser Thr Lys Val Asp Lys Lys Ile
                85                  90                  95

Ala Lys Thr Thr Pro Pro Ser Val Tyr Pro Leu Ala Pro Gly Ser Ala
            100                 105                 110

Ala Gln Thr Asn Ser Met Val Thr Leu Gly Cys Leu Val Lys Gly Tyr
        115                 120                 125

Phe Pro Glu Pro Val Thr Val Thr Trp Asn Ser Gly Ser Leu Ser Ser
    130                 135                 140

Gly Val His Thr Phe Pro Ala Val Leu Glu Ser Asp Leu Tyr Thr Leu
145                 150                 155                 160

Ser Ser Ser Val Thr Val Pro Ser Ser Pro Arg Pro Ser Glu Thr Val
                165                 170                 175

Thr Cys Asn Val Ala His Pro Ala Ser Ser Thr Lys Val Asp Lys Lys
            180                 185                 190

Ile Glu Pro Arg Gly Pro Thr Ile Lys Pro Cys Pro Pro Cys Lys Cys
        195                 200                 205

Pro Ala Pro Asn Leu Leu Gly Gly Pro Ser Val Phe Ile Phe Pro Pro
    210                 215                 220

Lys Ile Lys Asp Val Leu Met Ile Ser Leu Ser Pro Ile Val Thr Cys
```

-continued

```
225                 230                 235                 240
Val Val Val Asp Val Ser Glu Asp Asp Pro Asp Val Gln Ile Ser Trp
            245                 250                 255

Phe Val Asn Asn Val Glu Val His Thr Ala Gln Thr Gln Thr His Arg
            260                 265                 270

Glu Asp Tyr Asn Ser Thr Leu Arg Val Val Ser Ala Leu Pro Ile Gln
        275                 280                 285

His Gln Asp Trp Met Ser Gly Lys Glu Phe Lys Cys Lys Val Asn Asn
        290                 295                 300

Lys Asp Leu Pro Ala Pro Ile Glu Arg Thr Ile Ser Lys Pro Lys Gly
305                 310                 315                 320

Ser Val Arg Ala Pro Gln Val Tyr Val Leu Pro Pro Pro Glu Glu Glu
            325                 330                 335

Met Thr Lys Lys Gln Val Thr Leu Thr Cys Met Val Thr Asp Phe Met
            340                 345                 350

Pro Glu Asp Ile Tyr Val Glu Trp Thr Asn Asn Gly Lys Thr Glu Leu
        355                 360                 365

Asn Tyr Lys Asn Thr Glu Pro Val Leu Asp Ser Asp Gly Ser Tyr Phe
        370                 375                 380

Met Tyr Ser Lys Leu Arg Val Glu Lys Lys Asn Trp Val Glu Arg Asn
385                 390                 395                 400

Ser Tyr Ser Cys Ser Val Val His Glu Gly Leu His Asn His His Thr
            405                 410                 415

Thr Lys Ser Phe Ser Arg Thr Pro Gly Lys
            420                 425
```